US009779862B2

(12) United States Patent
Ishikawa et al.

(10) Patent No.: US 9,779,862 B2
(45) Date of Patent: Oct. 3, 2017

(54) MAGNETIC SUBSTANCE AND MAGNETIC SUBSTANCE MANUFACTURING METHOD

(71) Applicants: IHI Corporation, Tokyo (JP); Yoshihiro Ishikawa, Tokyo (JP)

(72) Inventors: Yoshihiro Ishikawa, Tokyo (JP); Haruki Eguchi, Tokyo (JP)

(73) Assignees: IHI Corporation, Tokyo (JP); Yoshihiro Ishikawa, Tokyo (JP)

( * ) Notice: Subject to any disclaimer, the term of this patent is extended or adjusted under 35 U.S.C. 154(b) by 175 days.

(21) Appl. No.: 14/739,217

(22) Filed: Jun. 15, 2015

(65) Prior Publication Data

US 2015/0318095 A1 Nov. 5, 2015

Related U.S. Application Data

(63) Continuation of application No. PCT/JP2013/083519, filed on Dec. 13, 2013.

(30) Foreign Application Priority Data

Dec. 14, 2012 (JP) ................................ 2012-273951

(51) Int. Cl.
*H01F 1/42* (2006.01)
*A61K 31/295* (2006.01)

(52) U.S. Cl.
CPC ..................................... *H01F 1/42* (2013.01)

(58) Field of Classification Search
CPC ........................................................ H01F 1/42
See application file for complete search history.

(56) References Cited

U.S. PATENT DOCUMENTS

| | | | |
|---|---|---|---|
| 2010/0155649 A1 | 6/2010 | Han et al. | |
| 2015/0218095 A1* | 8/2015 | Ramanujulu ........ | C07D 209/14 514/275 |

FOREIGN PATENT DOCUMENTS

| | | | |
|---|---|---|---|
| JP | 2001011455 A | 1/2001 | |
| WO | 2009032967 A2 | 3/2009 | |

OTHER PUBLICATIONS

Miyasaka et al, "Single-Chain Magnet Behavior in an Alternated One-Diemensional Assembly of a MnIII Schiff-Base Complex and a TCNQ Radical", Chemistry a European Journal, 12, 2006, pp. 7028-7040.*
Petersen et al, "[MnII(t-Bu)4salen]2 and Its Reaction with TCNE", Journal of Solid State Chemistry, 159, 2011, pp. 403-406.*
Oshio et al, "Incorporation of MnIII and FeII Complexes into TCNQ Networks: Preparations, Crystal Strcutures and Magnetic Propetries of {MnIII(salen)(TCNQ).05]{MnIII(salen)(TCNQ)0. 5(CH3OH)]-CH3OH H2O and {FeII)CH3OH)4(TCNQ)2]TCNQ 2CH3CN", Bull. Chem. Soc. Jpn., 68, 1995, pp. 889-897.*
Oshio et al, "Structure and Magnetic Properties of {MnII-I(salen)(TCNQ)1/2], {FeII(CH3OH)4(TCNQ2](TCNQ),[CuII(tpa) (TCNQ)2]", The 44$^{th}$ Coordination Chemisty Symposium, Syllabus 2P34, Nov. 7, 1994.*
Oshio et al, "Incorporation of MnIII and FeII Complexes into TCNQ Networks: Preparations, Crystal Strcutures and Magnetic Propetries of {MnIII(salen)(TCNQ).05]{MnIII(salen)(TCNQ)0. 5(CH3OH)]-CH3OH H2O and {FeII)CH3OH)4(TCNQ)2]TCNQ 2CH3CN", Bull. Chem. Soc. Jpn., 68, 1995, pp. 889-897.*
B. R. Muller, et al "A New Ferrimagnetically Ordered Charge-transfer Complex based on high-spin iron(III) Chelate Tetracyanoethenide with a Tc of 10K", Journal of Magnetism and Magnetic Materials, Elsevier Science Publishers, Amsterdam, NL, vol. 246, No. 1-2, Apr. 1, 2002, pp. 283-289.
Hiroki Oshio, et al The 44th Coordination Chemistry Symposium, Syllabus 2P34, Nov. 7, 1994, 4 pages (including Japanese language).
H. Miyasaka et al "Single-chain Magnet Behavior in an Alternated One-Dimensional Assembly of a MnIII Schiff-base Complex and a TCNQ Radical", Chemistry—A European Journal., vol. 12, No. 27, Sep. 18, 2006, pp. 7028-7040.
EESR dated Jul. 7, 2016.
K. Suto, et al "Synthesis and Magnetic Properties of Anthracenes with Nitronyl Nitroxides and Their Metal Complexes", Faculty of Engineering, Hosei University and Institute of Molecular Science, 3 pages.

* cited by examiner

*Primary Examiner* — Carol M Koslow
(74) *Attorney, Agent, or Firm* — Brundidge & Stanger, P.C.

(57) ABSTRACT

[object] A magnetization technique that enhances magnetic properties of an organic compound is provided without damaging properties of the organic compound or while maintaining the structure of the organic compound.
[solution] The present disclosure is a method for manufacturing a magnetic substance composed of crystals of a magnetization target compound and an electron acceptor by combining the magnetization target compound with the electron acceptor; forming a solution by dissolving a mixture of the magnetization target compound and the electron acceptor in a solvent; maintaining the solution in a very low temperature state and allowing the solution to deposit the crystals of the magnetic target compound and the electron acceptor; and separating the crystals from the solvent.

3 Claims, 6 Drawing Sheets

(1)

(2)

(3)

MAGNETIC SUBSTANCE AND MAGNETIC SUBSTANCE MANUFACTURING METHOD

CROSS REFERENCE TO RELATED APPLICATION

This application is a Bypass-Continuation Application of PCT International Application No. PCT/JP2013/083519, filed Dec. 13, 2013, which claims priority from Japanese Patent Application No. 2012-273951, filed Dec. 14, 2012, the entire contents of which are incorporated herein by reference.

TECHNICAL FIELD

The present disclosure relates to a magnetic substance and a method for manufacturing the magnetic substance.

BACKGROUND ART

The applicant of the present application has found that it is possible to make an organic compound itself ferromagnetic by modifying the structure of the organic compound (Domestic Re-publication of PCT international Publication No. 2008-001851). Availability of the organic compound can be enhanced by making the organic compound ferromagnetic; and, for example, a medicine composed of an organic magnetic substance can be concentrated in a specific tissue or organ in a living body by applying the medicine to the living body and then applying a magnetic field to it. Consequently, medical effects are enhanced by increasing a drug concentration in an abnormal tissue. This leads to a reduction of the drug concentration at sites other than the abnormal tissue, so that side effects of the medicine on normal tissues can be reduced. Furthermore, in a field of semiconductors, performance of a semiconductor device can be enhanced by making an organic film magnetic. Examples of such a semiconductor device include switching elements and organic electroluminescence elements.

The applicant of the present application suggested a metal-salen complex compound as an organic magnetic substance compound (WO2010/058280). Since the metal-salen complex compound has an anticancer action, the metal-salen complex compound can be concentrated in cancer tissues by applying a magnetic field to cancer tissues of an individual. This can prevent expansion of the metal-salen complex compound to sites other than the cancer tissues, so that a cancer treatment system with little side effects can be realized. Furthermore, since the metal-salen complex compound combines with other medical compounds, it also functions as a magnetic carrier of other medical compounds. As examples of other organic magnetic compounds, there are forskolin described in Domestic Re-publication of PCT international Publication No. 2008-001851, and a PDE5 inhibitor.

The applicant of the present application focuses attention on the difference in density of electron spin electric charges of these organic compounds and reported that magnetic properties of an organic compound becomes higher as the difference in density of electron spin electric charges is higher. Specifically speaking, when the difference in density of electron spin electric charges of the organic compound changes due to modification of side chains and/or cross-linking of the side chains of the organic compound, the organic compound will become ferromagnetic even if it is a known compound.

CITATION LIST

Patent Literature

[PTL 1] Domestic Re-publication of PCT International Publication No. 2008-001851

[PTL 2] WO2010/058280

SUMMARY

Technical Problem

When the structure of an organic compound, which is not magnetic or stays paramagnetic, is intentionally modified with an attempt to make the organic compound magnetic or enhance the magnetic properties of the organic compound, this may sometimes turn out to damage properties of the organic compound. For example, changes in the structure of the organic compound may reduce medical effects of the organic compound or degrade physical properties of the organic compound.

So, it is an object of the present disclosure to provide a magnetization technique capable of enhancing magnetic susceptibility of a compound while maintaining the structure of the organic compound without damaging properties of the compound and obtain a ferromagnetic substance and a method for manufacturing the ferromagnetic substance by applying this magnetization technique to the compound.

Solution to Problem

As a result of earnest examinations in order to achieve the above-described object, the inventor of the present disclosure has found that a crystal structure formed when a magnetization target compound and an electron acceptor are crystallized at a very low temperature contributes to new acquisition of magnetic properties by the magnetization target compound or enhancement of magnetic susceptibility of the magnetization target compound.

When the magnetization target compound as an electron donor forms charge transfer complex crystals with the electron acceptor at the very low temperature, electrons move from the magnetization target compound to the electron acceptor. Then, as electric charge density of unpaired electrons in electron orbits of the magnetization target compound increases, the magnetic properties of the magnetization target compound are enhanced, that is, the magnetic susceptibility to the applied magnetic field is enhanced.

A series of disclosures according to the present application were devised based on such a finding; and a first disclosure is characterized by being a magnetic substance including a metal-salen complex compound as an organometal complex compound and an electron acceptor. Then, a second disclosure is a magnetic substance including a magnetization target compound and an electron acceptor and is characterized in that the magnetization target compound has electrons to be donated to the electron acceptor; and when the magnetization target compound and the electron acceptor form multicomponent crystals of a charge transfer complex at a very low temperature and the electrons are donated from the magnetization target compound to the electron acceptor, magnetic susceptibility of the magnetization target compound is enhanced.

Furthermore, a third disclosure is a magnetic substance manufacturing method characterized in that a solution is formed by dissolving a mixture of the magnetization target compound and the electron acceptor in a solvent, the solution is maintained in a very low temperature state and made to deposit crystals of the magnetic target compound and the electron acceptor, and the crystals are separated from the solvent and thereby formed into a magnetic substance.

Advantageous Effects of Disclosure

According to the present disclosure, magnetization of the magnetization target compound or enhancement of the magnetic susceptibility of the magnetization target compound can be achieved while maintaining the structure of the magnetization target compound without damaging specific properties of the compound.

DESCRIPTION OF EMBODIMENTS

Figure 1:
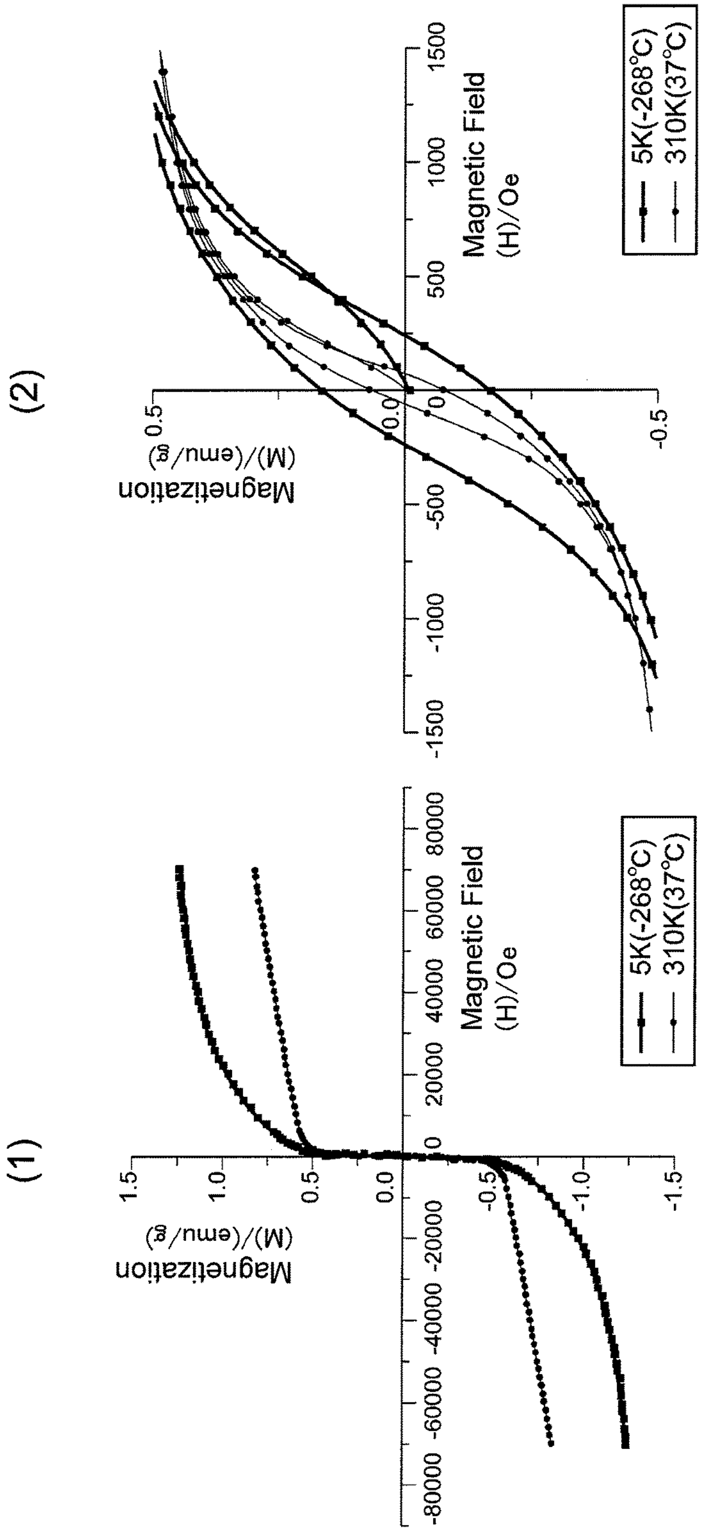
FIGS. 1(1) and 1(2) show magnetic field-magnetization curves of magnetic substances according to the present disclosure.

There is no limitation on the magnetization target compound of the present disclosure as long as it can be magnetized by an electron donor. For example, the aforementioned metal-salen complex is preferred. The magnetization target compound may be derivatives of a metal-salen complex and composites of the metal-salen complex combined with other medical compounds (WO2010/058280), or multimers of an organic metal-salen complex (Japanese Patent Application Laid-Open (Kokai) Publication No. 2009-256232, Japanese Patent Application Laid-Open (Kokai) Publication No. 2009-256233, and WO/2012/144634). Also, the magnetization target compound may be the aforementioned forskolin or PDE5 inhibitor.

Furthermore, the magnetization target compound may be the following new metal-salen complex compound or metal-salen complex derivatives (PCT/JP20121062301).

New Metal-Salen Complex Compound (I)

(I)

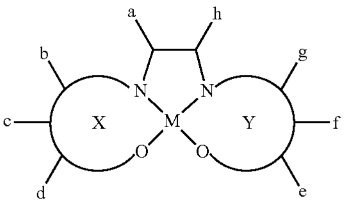

Each of X and Y is a five-membered ring structure including a coordinate bond between N and M, or its six-membered ring structure, wherein M is a bivalent metallic element composed of Fe (iron), Cr (chromium), Mn (manganese), Co (cobalt), Ni (nickel), Mo (molybdenum), Ru (rubidium), Rh (rhodium), Pd (palladium), W (tungsten), Re (rhenium), Os (osmium), Ir (iridium), Pt (platinum), Nd (niobium), Sm (samarium), Eu (europium) or Gd (gadolinium). If both X and Y are the five-membered ring structure, b and g do not exist and Formula (I) is any one of (i) to (iv) below.

(i) Each of a to h is hydrogen or any one of (A) to (G) mentioned below and —C(═O)m (where m is hydrogen or any one of (A) to (G) mentioned below);

(ii) each of (c, d) and (f, e) forms part of a heterocyclic structure and constitutes a condensate of the compound represented by Formula (I) and the heterocyclic structure, each of a, b, g, and h is hydrogen or any one of (A) to (G) mentioned below and —C(═O)m (where m is hydrogen or any one of (A) to (G) mentioned below), the heterocyclic structure is any one of three-membered to seven-membered ring structures containing furan, theophene, pyrrole, pyrrpyrrolidine, pyrazole, pyrazolone, imidazole, 2-isoimidazole, oxazole, isoxazole, thiazole, imidazole, imidazolidine, oxazoline, oxazolidine, 1,2-pyran, thiazine, pyridine, pyridazine, pyrimidine, pyrazine, orthoxadine, oxazine, piperidine, piperazine, triazine, dioxane, and morpholine, and a side chain for the heterocyclic structure is halogen, —R,—O—R (where R is one functional group selected from a hydrocarbon group including a methyl group), or hydrogen;

(iii) each of (c, d) and (f, e) forms part of one of condensed ring structures containing benzene or naphthalene and anthracene and forms a condensate of the compound represented by Formula (I) and the condensed ring structure, each of a, b, g, and h is hydrogen or any one of (A) to (G) mentioned below, and a side chain for the condensed ring structure is halogen, R—O—: (where R is one functional group selected from a hydrocarbon group including a methyl group), or hydrogen;

(iv) each of a and h forms part of a cyclic hydrocarbon structure containing a compound mentioned below and forms a condensate of the compound represented by Formula (I) and the cyclic hydrocarbon structure

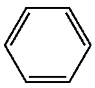

or

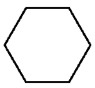

a side chain for each of b to g and the cyclic hydrocarbon structure is hydrogen or any one of (A) to (G) mentioned below.

(A) $—CO_2R$,—C(═O)R (where R represents hydrogen or chain or cyclic hydrocarbon having a saturated structure with carbon number 1 to 6 or an unsaturated structure (alkane or alkyne))

(B) $—CO(OCH_2CH_2)_2OCH_3$ (C)

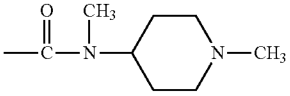

-continued (D)

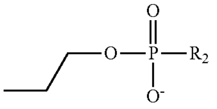

(where $R_2$ represents one of nucleic acids which are formed of adenine, guanine, thymine, cytosine, or uracil, or a plurality of the nucleic acids which are combined together);

(E) —NHCOH or —$NR_1R_2$ (where $R_1$ and $R_2$ represent hydrogen or chain or cyclic hydrocarbon with the same or different saturated structure with carbon number 1 to 6 or unsaturated structure (alkane or alkyne));

(F) —$NHR_3$—,—$NHCOR_3$,—$CO_2$—$R_3$,—S—S—$R_3$ or —$R_3$ (where $R_3$ represents hydrogen or a substituted compound condensed as a result of elimination of a leaving group such as a hydroxyl group; and the substituted compound is functional molecules including at least one of enzymes, antibodies, antigens, peptides, amino acids, oligonucleotides, proteins, nucleic acids, and medical molecules); and (G) halogen atoms such as chlorine, bromine, or fluorine.

Preferred embodiments of a self-magnetic metal-salen complex compound represented by Formula (I) are (II) to (XI) below.

(II)

X, Y: six-membered ring structure (a to h)=H

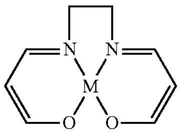

(III)

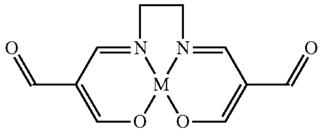

X, Y: six-membered ring structure (c, f)=C(O)H (a, b, d, e, g, h)=H (IV)

X, Y: five-membered ring structure, (a, c, d, e, f, h)=H

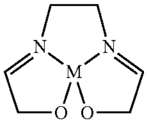

(V)

X, Y: six-membered ring structure (a, b, g, h): H (e, f), (g, h): constitute part of furan and furan is condensed with a main skeleton.

M: Fe

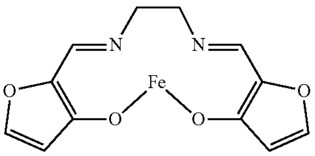

(VI)

X, Y: six-membered ring structure (a, h): constitute part of cyclohexane and cyclohexane is condensed with a main skeleton.

(c, d), (e, f): constitute benzene (b, g): H

M: Fe

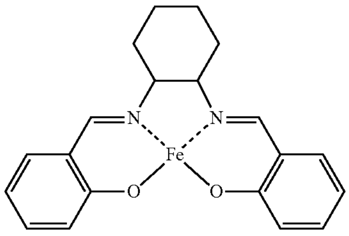

(VII)

X, Y: six-membered ring structure (a, h): constitute part of benzene (c, d), (e, f): constitute benzene (b, g): H M: Fe

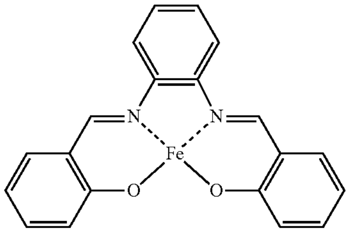

(VIII)

X, Y: six-membered ring structure (c, d), (e, f): constitute anthracene (a, b, g, h): H M: Fe

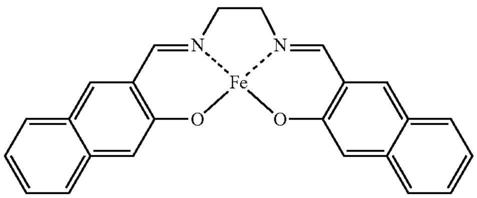

(IX)

X, Y: six-membered ring structure (c, d), (e, f): constitute anthracene (a, b, g, h)=H
Isomer of (V)
M: Fe

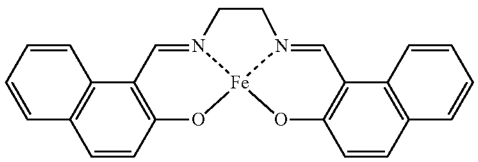

(X)
X, Y: six-membered ring structure
(c, d), (e, f): constitute benzene
Side chains at meta positions of benzene are halogens (bromine)
(a, b, g, h): H
M: Fe

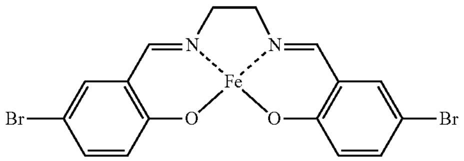

(XI)
X, Y: six-membered ring structure
(c, d), (e, f): constitute benzene
Side chains at meta positions of benzene are methoxyl groups.
(a, b, g, h): H
M: Fe

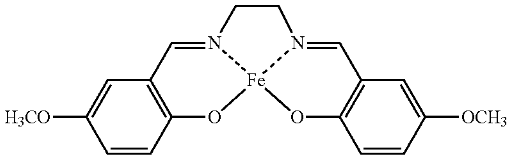

The magnetization target compound may be any compound as long as it forms crystals of an electron acceptor and a charge transfer complex and its magnetic susceptibility may be enhanced remarkably after generation of the crystals as compared to the magnetic susceptibility before the generation of the crystals (the magnetic properties after the generation of the crystals should be enhanced to 1.5 times higher than those before the generation of the crystals). This type of magnetization target compound may be any compound as long as it has electrons to be donated to the electron acceptor and the donation of the electrons may increase the electric charge density of unpaired electron spins. The magnetization target compound has electron pairs which are not shared by other compounds; and as one electron moves to the electron acceptor, the magnetic susceptibility is enhanced.

Multicomponent crystals of a charge transfer complex are formed by dissolving the electron acceptor and the magnetization target compound in the solvent and causing crystallization at a very low temperature. The solvent should preferably be an organic solvent such as acetone or acetonitrile. In order to make the multicomponent crystals easily separable from the solvent, a boiling point of the solvent should preferably be a normal temperature or about a room temperature or lower.

The very low temperature is minus 60 degrees Celsius, preferably minus 70 degrees Celsius, or more preferably minus 80 degrees Celsius. In order to make the multicomponent crystals separable from the solvent, the temperature should preferably be as low as possible unless the solvent solidifies. A cooling speed to achieve the very low temperature environment should preferably be controlled so that the crystals of the electron acceptor and the magnetization target compound can be formed. When the cooling speed is higher than necessary or, on the contrary, lower than necessary, the crystals may not be generated or not grow. So, the cooling speed should preferably be 1° C./min or lower.

Known techniques that promote crystallization of compounds utilize the environment where crystalline nuclei can be easily formed. Any known means for forming the crystalline nuclei is used by the disclosures of the present application. For example, such means includes controlling the speed to cool the mixture of the magnetization target compound and the electron acceptor as described above and applying vibrations. The cooling speed does not have to be constant; and the cooling speed may be low at an initial stage of crystallization so that the crystalline nucleus can be easily formed; and the cooling speed can be increased after waiting for the time when the crystalline nuclei are formed.

The electron acceptor may be any substance as long as it can accept electrons from the magnetization target organic compound and form crystals with the magnetization target organic compound; and examples of the electron acceptor include tetracyanoquinodimethane (TCNQ), tetracyanoethylene (TCNE), and anthryl derivatives: 9-anthryl nitronyl nitroxide compounds (10-(2-methyl-1-butoxy)-9-anthryl nitronyl nitroxide, 10-ethoxy-9-anthryl nitronyl nitroxide, and 10-methoxy-9-anthryl nitronyl nitroxide).

It is desirable in terms of formation of the multicomponent crystals of the electron acceptor and the magnetization target compound that a molar ratio of the electron acceptor to the magnetization target compound should be 1:1. A crystal structure of the electron acceptor and the magnetization target compound should preferably be needle crystals in order for the multicomponent crystals to be capable of exhibiting the magnetic properties. The magnetic properties of the multicomponent crystals should preferably be saturation magnetization of, for example, 3.0 emu/g or more to the degree allowing the multicomponent crystals to be guided to a magnetic field from outside the body of an individual such as a human after application of the magnetic field.

The magnetic substance according to the present disclosure can be used, for example, as a medicine guided to a target location by a magnetic field applied externally For example, a metal-salen complex can be used as an antitumor agent based on its anticancer effects and also can be used as a switching element (Japanese Patent Application No. 2008-137895), an organic electroluminescence element (Japanese Patent Application No. 2010-16081), and an electric double-layered capacitor (PCT/JP2012/60708).

EXAMPLES

Example 1

Synthesis of Metal Salen (Iron Salen)

Step 1:

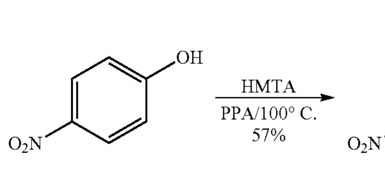

$C_6H_5NO_3$
Mol. Wt.: 139.11
1
25 g $C_7H_5NO_4$
Mol. Wt.: 167.12
2
17 g

A mixture of 4-nitrophenol (25 g, 0.18 mol), hexamethylene tetramine (25 g, 0.18 mol), and polyphosphoric acid (200 ml) were stirred for one hour at the temperature of 100 degrees Celsius. Then, that mixture was introduced to 500 ml of ethyl acetate and 1 L of water and stirred until it completely dissolved. Furthermore, when 400 ml of ethyl acetate was added to that solution, the solution separated into two phases. Subsequently, an aqueous phase was removed from the solution; and the remaining compound was washed twice with a basic solvent and dried over anhydrous $MgSO_4$. As a result, 17 g of Compound 2 (57% yield) was synthesized.

Step 2:

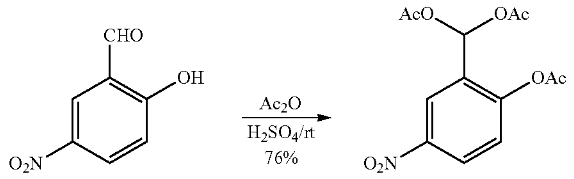

$C_7H_5NO_4$
Mol. Wt: 157.12
2
17 g $C_{13}H_{13}NO_8$
Mol. Wt: 311.24
3
24 g

Compound 2 (17 g, 0.10 mol), acetic anhydride (200 ml) and $H_2SO_4$ (minimal) were stirred for one hour at room temperature. The resulting solution was mixed for 0.5 hour in iced water (2 L) to bring about hydrolysis. The resulting solution was filtered and dried in air, thereby obtaining white powder. The powder was recrystallized, using a solvent containing ethyl acetate. As a result, 24 g of Compound 3 (76% yield) was obtained in the form of white crystals.

Step 3:

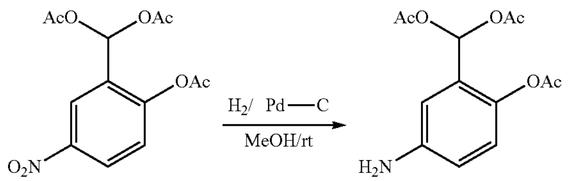

$C_{13}H_{13}NO_8$
Mol. Wt.: 311.24
3
24 g $C_{13}H_{15}NO_6$
Mol. Wt.: 231.26
4
21 g

A mixture of carbon (2.4 g) supporting 10% palladium with Compound 3 (24 g, 77 mmol) and methanol (500 ml) was reduced over night in a 1.5 atm hydrogen reducing atmosphere. After the reduction was completed, the product was filtered, thereby allowing Compound 4 (21 g) in the form of brown oil to be synthesized.

Step 4, 5:

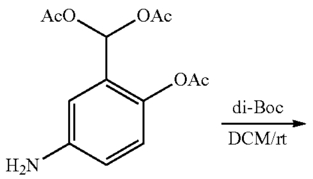

$C_{13}H_{15}NO_6$
Mol. Wt.: 231.26
4
21 g

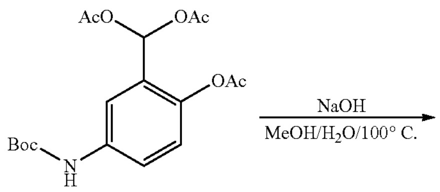

$C_{16}H_{23}NO_5$
Mol. Wt.: 381.36
5
58%

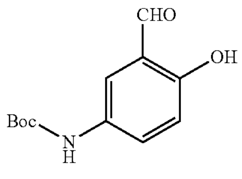

$C_{12}H_{15}NO_4$
Mol. Wt.: 237.25
6
10 g

Compound 4 (21 g, 75 mmol) and di(tert-butyl) dicarbonate (18 g, 82 mmol) were stirred over night in anhydrous dichloromethane (DCM) (200 ml) in a nitrogen atmosphere. The resulting solution was allowed to evaporate in a vacuum and then dissolved in methanol (100 ml). Sodium hydroxide (15 g, 374 mmol) and water (50 ml) were then added and the solution was brought to reflux for 5 hours. The solution was then cooled, filtered, washed with water, and allowed to dry in a vacuum, thereby obtaining a brown compound. The resulting compound was processed twice by flash chromatography using silica gel, thereby obtaining 10 g of Compound 6 (58% yield).

Step 6:

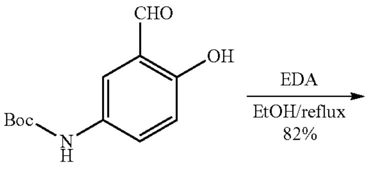

$C_{12}H_{15}NO_4$
Mol. Wt.: 237.25
6
10g

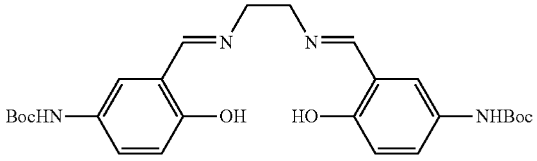

$C_{26}H_{34}N_4O_6$
Mol. Wt.: 498.57
7
8.5g

Compound 6 (10 g, 42 mmol) was introduced into 400 ml of anhydrous ethanol, the mixture was brought to reflux while heated, and several drops of ethylene diamine (1.3 g, 21 mmol) were added into 20 ml of anhydrous ethanol while stirred for 0.5 hour. The mixture was introduced into a container of ice, where it was cooled and mixed for 15 minutes. It was then washed with 200 ml of ethanol, filtered, and dried in a vacuum, thereby obtaining 8.5 g of Compound 7 (82% yield).

Step 7:

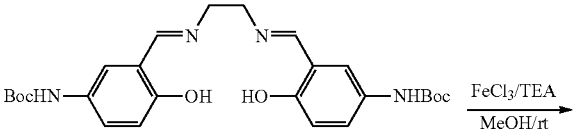

$C_{29}H_{34}N_4O_6$
Mol. Wt.: 498.57
7
8.2 g

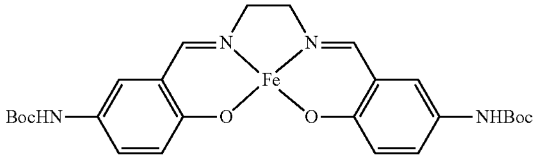

Complex A
5.7 g

Compound 7 (8.2 g, 16 mmol) and triethylamine (22 ml, 160 mmol) were introduced into dehydrated methanol (50 ml) and the obtained solution was mixed with a solution of $FeCl_3$ (2.7 g, 16 mmol) added in 10 ml methanol in a nitrogen atmosphere. The ingredients were mixed for one hour in the nitrogen atmosphere at the room temperature, thereby obtaining a brown compound. Subsequently, this compound was then dried in a vacuum. The resulting compound was diluted with 400 ml of dichloromethane, washed twice with a basic solution, and dried in a vacuum, thereby obtaining complex A. The resulting compound was recrystallized in a solution of diethyl ether and paraffin, and assay by high-speed liquid chromatography revealed that 5.7 g of complex A (iron-salen complex compound) of purity of 95% or higher was obtained (62% yield).

Example 2

Synthesis of TCNE and Iron-Salen Complex Multicomponent Crystals

Thirty mmol (5 ml) of the above-mentioned complex A (iron-salen complex) and 30 mmol (5 ml) of tetracyanoethylene (TCNE) (manufactured by Sigma-Aldrich) were dissolved in acetonitrile and the obtained solution was cooled by an ultra-deep freezer (manufactured by Sanyo) from a room temperature to minus 80 degrees Celsius for one hour, thereby causing crystallization of the iron-salen complex and TONE. Then, as a result of concentration of a container of acetonitrile, including multicomponent crystals (AAA mentioned below) of the iron-salen complex and TCNE, at 50° C. by an evaporator, 120 mg of multicomponent crystals were obtained. Acetonitrile was used as a solvent.

As a result of observation, the multicomponent crystals were dark brown.

AAA

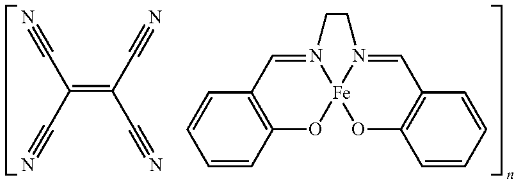

It is desirable that n should be 10 or more (the same applies hereinafter).

Example 3

Synthesis of 10-(2-methyl-1-butoxy)-9-anthryl nitronyl nitroxide was performed according to the following reaction formulae.

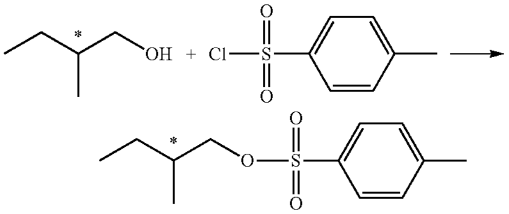

19

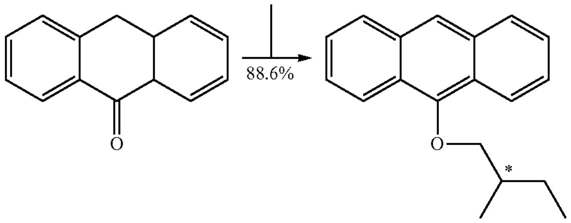

4 20

-continued

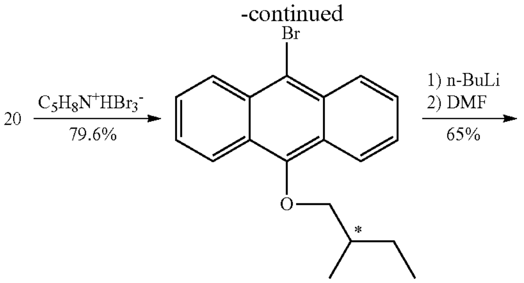

21

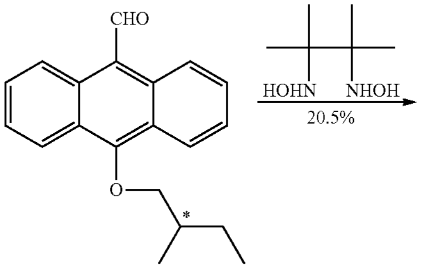

22

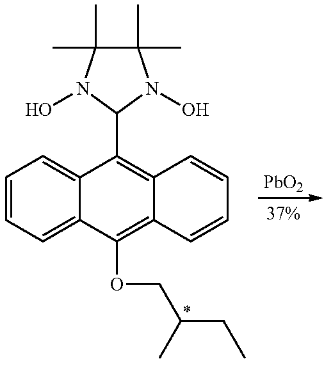

23

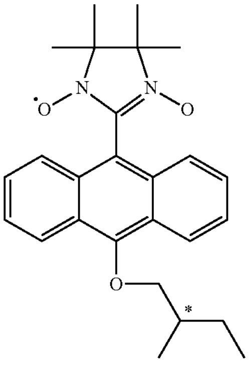

3

Overall yield 3.5%

Detailed explanations will be given below. (S)-(−)-2-methyl-1-butanol) (1.77 g, 20 mmol) and p-toluenesulfonyl chloride (3.81 g, 20 mmol) were dissolved in 35 ml of pyridine and the obtained solution was stirred at a normal temperature for 4 hours and cold water was added to it to stop the reaction. The solution was extracted with diethyl ether, dried with anhydrous magnesium sulfate, filtered, vacuum-concentrated, and dried with a vacuum pump, thereby synthesizing 3.53 g of Compound (19) at 73% yield.

In a nitrogen atmosphere, 20 ml of $CH_3CN$ was used as a solvent and Compound (19) (1.21 g, 5 mmol), anthrone (4) (1.2 g, 6 mmol), and $K_2CO_3$ (0.7 g, 5 mmol) were added, and the mixture was stirred at 95° C. for one day. The temperature was returned to the room temperature and the solution was extracted with dichlormethane, dried with anhydrous magnesium sulfate, and filtered, and then 1.17 g of Compound (20), 9-(2-methyl-1-butoxy) anthracene, was thereby separated at 88.6% yield by means of silica gel column chromatography using hexane.

Next, Compound (21), 9-bromo-10-(2-methyl-1-butoxy) anthracene, was synthesized. In a nitrogen atmosphere, 45 ml of acetic acid was used as a solvent, Compound (20), 9-(2-methyl-1-butoxy)anthracene, (263 mg, 1 mmol) and pyridinium bromide perbromide (320 mg, 1 mmol) were added, and the obtained mixed solution was stirred for 30 minutes. The solution was neutralized with a $K_2CO_3$ solution, extracted with dichloromethane, dried, and filtered, and Compound (21), 9-bromo-10-(2-methyl-1-butoxy)anthracene, was thereby synthesized at 79.6% yield by means of silica gel column chromatography using hexane.

Furthermore, in an argon atmosphere, 6 ml of anhydrous THF was added to dried Compound (21), 9-bromo-10-(2-methyl-1-butoxy)anthracene (342 mg, 1 mmol); and when the temperature was reduced to −78° C., n-Bull (1.25 ml, 2 mmol) was quickly added to the mixture and the obtained solution was stirred for 5 minutes; DMF (0.3 ml, 4 mmol) was added to the solution, which was then stirred for 5 minutes; and the temperature was returned to the normal temperature and the solution was stirred for 10 minutes. Cold water was added to the solution to stop the reaction; and the solution was extracted with dichloromethane, dried, and filtered, and Compound 22, 10-(2-methyl-1-butoxy)-9-anthraldehyde, was thereby synthesized at 65% yield by means of silica gel column chromatography at the ratio of hexane to dichloromethane being 2:1.

Next, 2-(10-methoxy-1-butoxy)-9-anthryl)-4,4,5,5-tetramethylimidazolidine-1,3-diol(23) was synthesized. In a nitrogen atmosphere, 9 ml of ethanol was used as a solvent, Compound 22, 10-(2-methyl-1-butoxy)-9-anthraldehyde (146 mg, 0.5 mmol), 2,3-dimetyl-2,3-dinitrobutane (222 mg, 1.5 mmol), and 2.3-dimetyl-2,3-dinitrobutane sulfate salt (74 mg, 0.3 mmol) were added, and the obtained mixture was stirred at 60° C. over night. The mixture was neutralized with a cooled aqueous solution of $K_2CO_3$ and filtered and residues were washed with hexane, thereby synthesizing 2-(10-methoxy-1-butoxy)-9-anthryl)-4,4,5,5-tetramethylimidazolidine-1,3-diol(23) at 20.5% yield.

A small amount of $K_2CO_3$, 2-(10-methoxy-1-butoxy)-9-anthryl)-4,4,5,5-tetramethylimidazolidine-1,3-diol(23) (110 mg, 0.26 mmol), and $PbO_2$ (3.8 g, 16.2 mmol) were added to 35 ml of acetone which was cooled to 0° C.; and the mixture was stirred for 15 minutes, $PbO_2$ was filtered out, and then Compound (3), 10-(2-methyl-1-butoxy)-9-anthryl-nitronyl nitroxide, was synthesized at 37% yield by means of silica gel column chromatography using diethyl ether.

Example 4

After 30 mmol (5 ml) of complex A (iron-salen complex) and 30 mmol (5 ml) of 10-(2-methyl-1-butoxy)-9-anthryl-nitronyl nitroxide were dissolved in a heptane solution, crystals (BBB) were obtained in the same manner as Example 2,

BBB

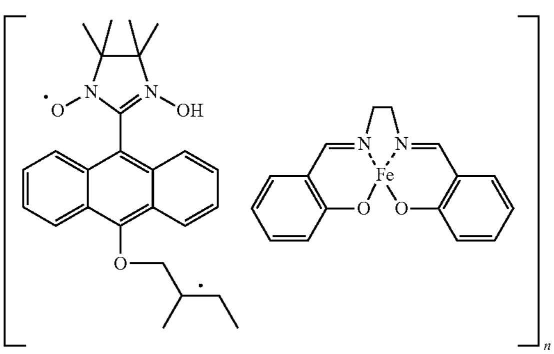

As a result of observation, the multicomponent crystals were dark brown.

Example 5

10-Ethoxy-9-anthryl nitronyl nitroxide was synthesized according to the following reaction formulae.

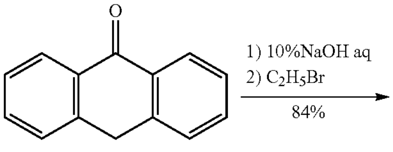

4

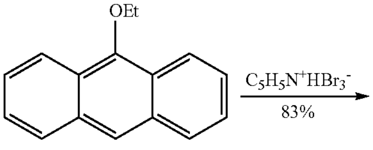

15

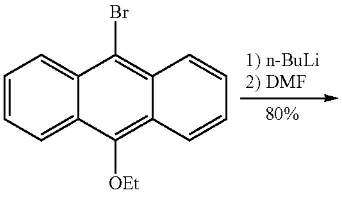

16

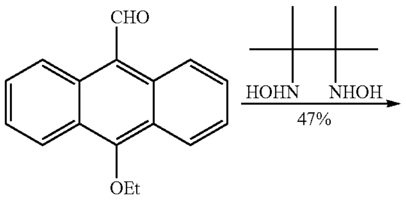

17

-continued

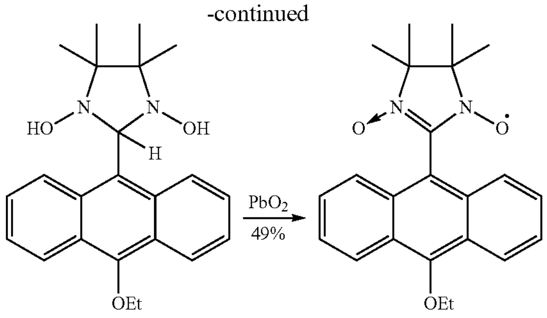

18

2

Overall yield 13%

In a nitrogen atmosphere, Alfa Aesar-made anthrone (4) (1.5 g, 7.5 mmol) was dissolved in 75 ml of THF, an aqueous solution of 10% NaOH (7.5 ml) was added, and the obtained solution was stirred for 30 minutes; and then 7.5 ml of ethyl bromide was added to the solution, which was then stirred for 30 minutes. Subsequently, the solution was stirred for one day in an oil bath at 50° C. Water was added to it to stop the reaction. The solution was extracted with dichloromethane, dried, filtered, separated by means of silica gel column chromatography at the ratio of hexane to dichloromethane being 1:1, and then recrystallized with pentane, thereby synthesizing 9-etoxyanthracene (15) at 84% yield.

Next, 45 ml of acetic acid was used as a solvent, 9-etoxyanthracene (15) (208 mg, 1 mmol) and pyridinium bromide perbromide (0.99 g, 3 mmol) were added, and the obtained mixture was stirred at 30° C. for 30 minutes. Water was added to it, crystals were deposited, and the solution was filtered, extracted with dichloromethane, dried, and filtered, and then 9-bromo-10-ethoxyanthracene(16) was synthesized at 83% yield by means of silica gel column chromatography using hexane.

Furthermore, in an argon atmosphere, 12 ml of anhydrous THF was added to dried 9-bromo-10-ethoxyanthracene(16) (600 mg, 2 mmol); and when the temperature was reduced to −78° C., n-Buli (2.5 ml, 4 mmol) was quickly added and the obtained solution was stirred for 5 minutes; and then DMF (0.6 ml, 8 mmol) was added, the solution was stirred for 5 minutes; and after the temperature was returned to the normal temperature, the solution was stirred for 10 minutes. Cold water was added to stop the reaction, the solution was extracted with dichloromethane, dried, and filtered, and then 10-ethoxy-9-anthraldehyde(17) was synthesized at 80% yield by means of silica gel column chromatography at the ratio of hexane to dichloromethane being 2:1.

Next, 2-(10-ethoxy-9-anthryl)-4,4,5,5-tetramethylimidazolidine-1,3-diol(18) was synthesized. In a nitrogen atmosphere, 9 ml of ethanol was used as a solvent, 10-ethoxy-9-anthraldehyde(17) (125 mg, 0.5 mmol), 2,3-dimetyl-2,3-dinitrobutane (222 mg, 1.5 mmol), and 2.3-dimetyl-2,3-dinitrobutane sulfate salt (74 mg, 0.3 mmol) were added, and the obtained mixture was stirred at 60° C. overnight. The mixture was neutralized with a cooled aqueous solution of $K_2CO_3$, the obtained solution was filtered, and residues were washed with hexane, thereby synthesizing 2-(10-ethoxy-9-anthryl)-4,4,5,5-tetramethylimidazolidine-1,3-diol(18) at 47% yield.

Lastly, 25 ml of dichloromethane was used as a solvent, 2-(10-ethoxy-9-anthryl)-4,4,5,5-tetrmetramethylimidazolidine-1,3-diol(18) (100 mg, 0.27 mmol) and $PbO_2$ (3.8 g, 16.2 mmol) were stirred for 30 minutes, and $PbO_2$ was filtered out. Then, the solution was concentrated with an evaporator and 10-ethoxy-9-anthryl nitronyl nitroxide (2) was synthesized at 49% yield by means of silica gel column chromatography using diethyl ether.

Example 6

Synthesis of 10-(2-ethoxy-1-butoxy)-9-anthryl nitronyl nitroxide and iron-salen complex multicomponent crystals Thirty mmol (5 ml) of complex A (iron-salen complex) and 30 mmol (5 ml) of 10-ethoxy-9-anthryl nitronyl nitroxide were dissolved in a heptane solution and crystals (CCC) were obtained by the same processing as that in Example 4. As a result of observation, the multicomponent crystals were dark brown.

CCC

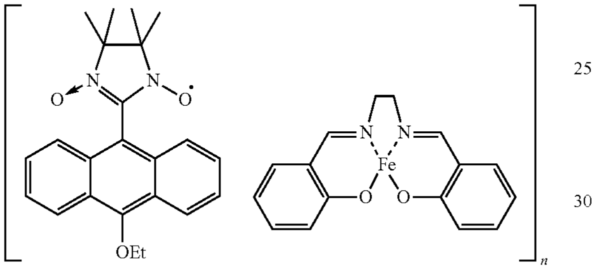

Example 7

10-Methoxy-9-anthryl nitronyl nitroxide (1) was synthesized according to the following reaction formulae.

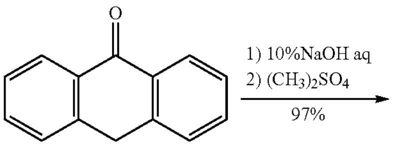

4

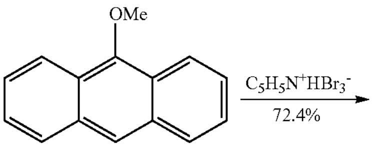

5

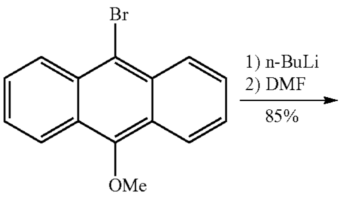

6

-continued

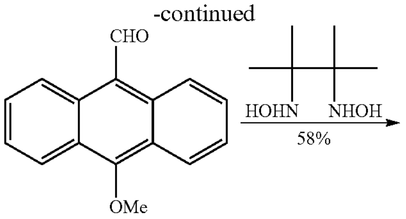

7

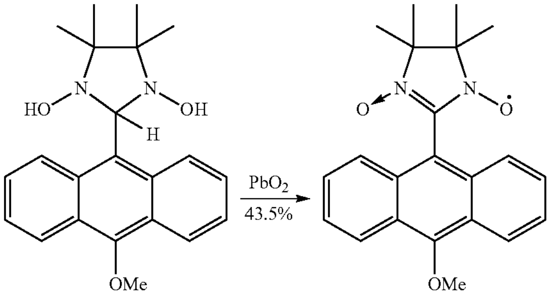

8 1

Overall yield 15%

In a nitrogen atmosphere, Alfa Aesar-made anthrone (4) (1.5 g, 7.5 mmol) was dissolved in 75 ml of THF, an aqueous solution of 10% NaOH (7.5 ml) was added, and the obtained solution was stirred for 30 minutes; and then dimethyl sulfate (0.5 ml, 5 mmol) was added to the solution, which was then stirred for 30 minutes. The solution was stirred for 15 minutes in an oil bath at 50° C. and water was added to it to stop the reaction. The solution was extracted with dichloromethane, dried, and filtered, and then 9-methoxyanthracene (5) was synthesized at 97% yield by means of silica gel column chromatography using hexane.

Next, 15 ml of acetic acid was used as a solvent, 9-methoxyanthracene (5) (208 mg, 1 mmol) and pyridinium bromide perbromide (0.33 g, 1 mmol) were added, and the obtained mixture was stirred for 20 minutes at 50° C. Water was added to it to stop the reaction and crystals were deposited, and then the solution was filtered, extracted with dichloromethane, dried, and filtered, and then 9-bromo-10-methoxyanthracene(6) was synthesized at 72.4% yield by means of silica gel column chromatography using hexane.

Furthermore, in an argon atmosphere, 6 ml of anhydrous THF was added to dried 9-bromo-10-methoxyanthracene(6) (287 mg, 1 mmol); and when the temperature was reduced to −78° C., n-Buli (1.25 ml, 2 mmol) was quickly added and the mixed solution was stirred for 5 minutes; DMF (0.3 ml, 4 mmol) was added to it and the solution was stirred for 5 minutes; and after the temperature was returned to the normal temperature, the solution was stirred for 10 minutes. Cold water was added to stop the reaction, the solution was extracted with dichloromethane, dried, and filtered, and then 10-methoxy-9-anthraldehyde(7) was synthesized at 85% yield by means of silica gel column chromatography at the ratio of hexane to dichloromethane being 2:1.

Next, 2-(10-methoxy-9-anthryl)-4,4,5,5-tetramethylimidazolidine-1,3-diol(8) was synthesized. In a nitrogen atmosphere, 9 ml of ethanol was used as a solvent, 10-methoxy-9-anthraldehyde(7) (118 mg, 0.5 mmol), 2,3-dimetyl-2,3-dinitrobutane (222 mg, 1.5 mmol), and 2.3-dimetyl-2,3-dinitrobutane sulfate salt (74 mg, 0.3 mmol) were added, and the obtained mixed solution was stirred at 60° C. overnight. The solution was neutralized with a cooled aqueous solution of $K_2CO_3$ and filtered and residues were washed with hexane, thereby synthesizing 2-(10-methoxy-9-anthryl)-4,4,5,5-tetramethylimidazolidine-1,3-diol(8) at 58% yield.

Lastly, 25 ml of dichloromethane was used as a solvent, 2-(10-methoxy-9-anthryl)-4,4,5,5-tetramethylimidazolidine-1,3-diol(8) (99 mg, 0.27 mmol) and $PbO_2$ (3.8 g, 16.2 mmol) were stirred for 30 minutes, and $PbO_2$ was filtered out; and then the solution was concentrated with an evaporator and 10-methoxy-9-anthryl nitronyl nitroxide (10-methoxy-9-anthrylnitronyl nitroxide)(1) was synthesized at 43.5% yield by means of silica gel column chromatography using diethyl ether.

Example 8

Synthesis of 10-ethoxy-9-anthryl nitronyl nitroxide and iron-salen complex multicomponent crystals Complex A (iron-salen complex) and 10-methoxy-9-anthryl nitronyl nitroxide were introduced into a heptane solution, the temperature was increased by 50° C., and the mixed solution was concentrated with an evaporator. As a result, a compound of chemical formulae (DDD) was synthesized. As a result of observation, the multicomponent crystals were dark reddish brown.

DDD

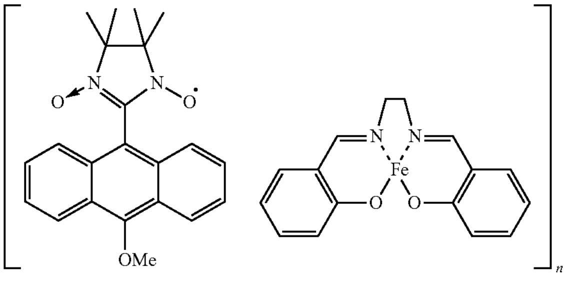

Example 9

Next, samples of crystals (the iron-salen complex compound—the electron acceptor) of the charge transfer complex of each example described above were prepared and the magnetic properties of the samples were measured. The magnetic properties measurement was conducted by applying a magnetic field to a measurement object to see whether or not the magnetic field would occur around the measurement object. Generally possible methods of the magnetic properties measurements are a dynamic method, an electromagnetic induction method, or a magnetic resonance method, or methods of, for example, superconducting quantum effects. In this example, a Superconducting Quantum Interference Device (SQUID), whose accuracy is the highest of these methods, were used. This SQUID is a sensitive magnetization measurement device and calculates a magnetization value of the sample by measuring slight changes of a magnetic flux penetrating through a superconducting loop device with Josephson junctions, as changes of a tunneling current passing through the junctions where the changes occur when the sample is moved. This method enables measurement of the relationship between the temperature and the magnetic properties under conditions of a ferromagnetic field of 7 Teslas (T) at maximum and high accuracy ($1\times10^{-8}$ emu).

As a result of the measurements, it was confirmed that the respective crystals had similar magnetic properties. Of these crystals, FIG. 1 show magnetization—magnetic field characteristic curves that are the results of measurements of magnetic field-magnetization curves of the crystals (AAA) of TCNE and the metal (iron) salen complex compound. FIG. 1(2) is an enlarged view of a hysteresis part of the characteristic curves in FIG. 1(1). It was found as can be seen from FIGS. 1(1) and 1(2) that the multicomponent crystals composed of the electron acceptor and the metal-salen complex compound had a hysteresis group which is a characteristic specific to a ferromagnetic substance. A measurement temperature was 310 K, which is a temperature almost close to a body temperature. Since the multicomponent crystals exhibited the magnetic properties and hysteresis further occurred at the temperature close to the body temperature, it was confirmed that the multicomponent crystals were a ferromagnetic substance.

Example 10

The following experiment was conducted using charge transfer complex magnetic crystals represented by AAA described above. An amount of the charge transfer complex crystals to the degree allowing their attraction to a magnet to be visibly observed was dissolved in physiological saline (30 mmol, 50 ml) when rat L6 cells were in a 30% confluent state; and then the obtained solution was sprinkled on a culture medium PBS and the state of the culture medium was photographed after 48 hours.

Figure 2:
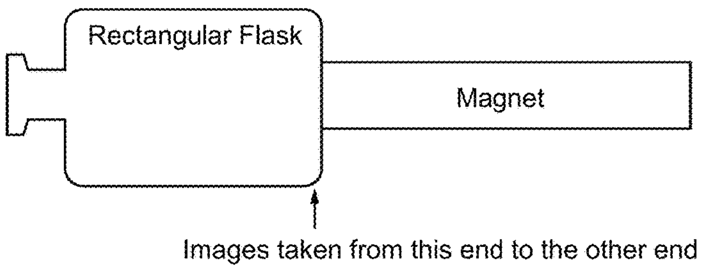
FIG. 2 is a block diagram illustrating the outline of an experiment system that verifies the location of a magnetic substance in a magnetic field.
Figure 3:
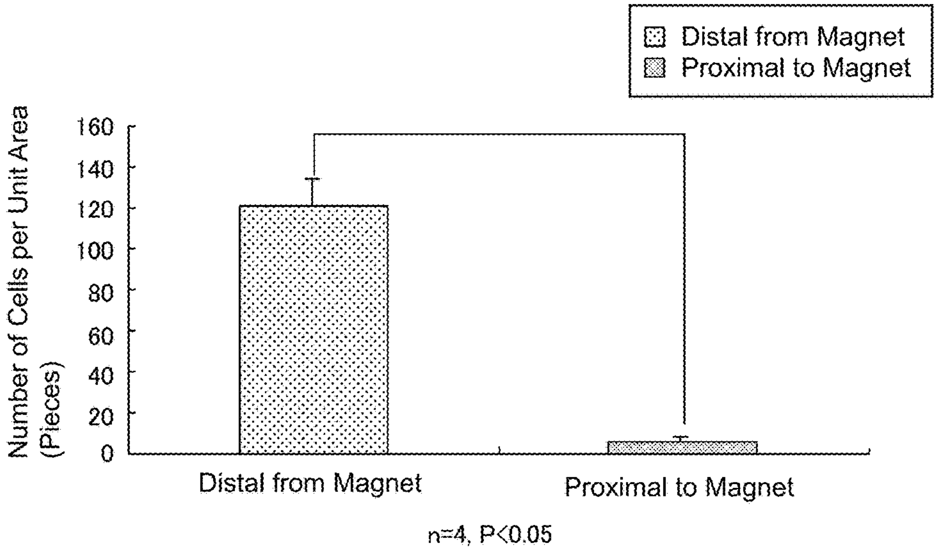
FIG. 3 is a characteristic diagram showing measurement results of changes in the number of cells based on variations of a concentration of the magnetic substance in the magnetic field.

FIG. 2 illustrates a state in which a bar magnet is in contact with a rectangular flask containing the rat L6 cell culture medium. Then, after 48 hours, an image of the bottom of the rectangular flask was photographed from one end to the other end and the number of cells was calculated and the results are shown in FIG. 3. Referring to FIG. 3, a proximal position from the magnet indicates within a project area of a magnet end face on the bottom of the rectangular flask and a distal position from the magnet indicates an area on the opposite side of the magnet end face on the bottom of the rectangular flask.

FIG. 3 shows that a concentration of the magnetic crystals increases as the magnetic crystals are attracted at the proximal position from the magnet; and it can be seen that the number of cells becomes extremely lower than that at the distal position due to a DNA breakage action of the metal-salen complex compound. As a result, the magnetic crystals can be concentrated at the target affected site or tissues of the individual by means of a system that combines the magnetic crystals and a magnetic means such as the magnet according to the present disclosure.

The magnetic crystals can be concentrated on a solid tissue by placing the tissue in this magnetic environment. After intravenously injecting the magnet crystals (magnetic crystals concentration: 5 mg/m (15 mmol)) to a mouse weighing about 30 g, a laparotomy was performed, and the mouse was placed on the iron plate to locate its right kidney between the pair of magnets.

Figure 4:
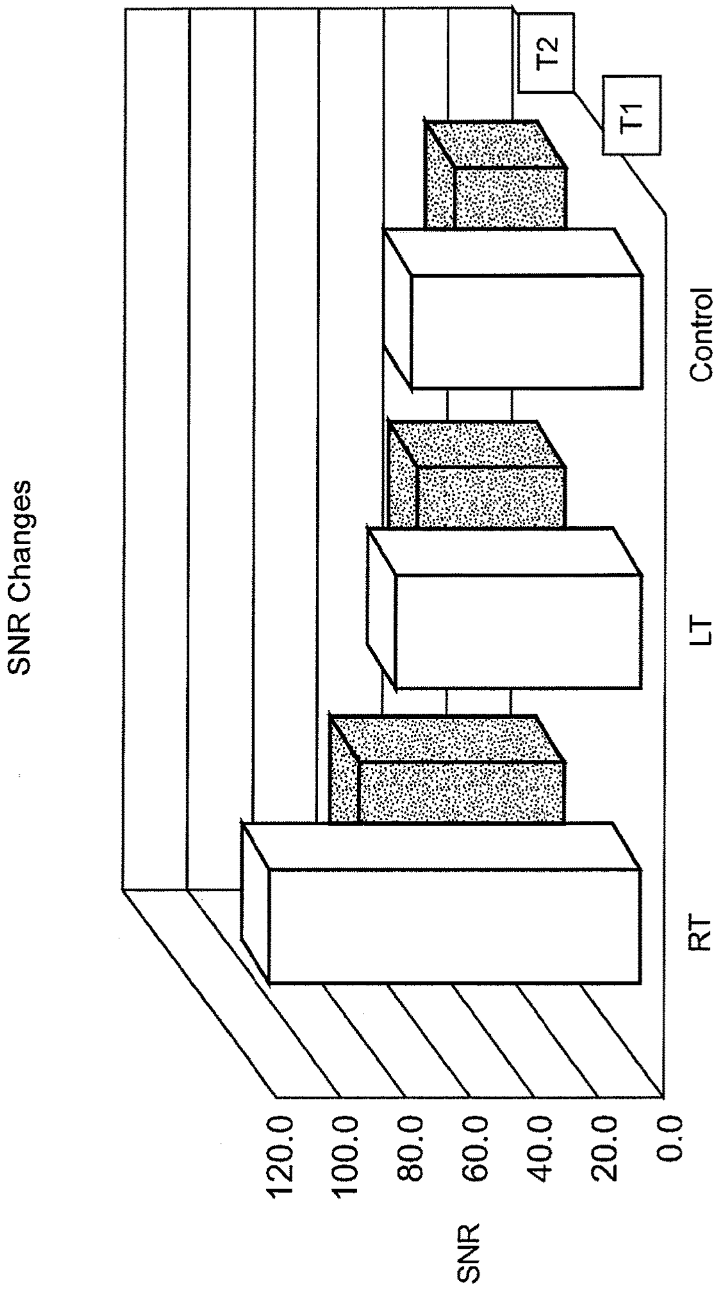
FIG. 4 is a graph of MRI measurement results (T1 enhanced signal) of the magnetic substance on a mouse's kidney.

The magnets used were Product No. N50 (neodymium permanent magnets) by Shin-Etsu Chemical Co., Ltd. with a residual flux density of 1.39 to 1.44 T. Under this circumstance, the magnetic field applied to the right kidney was about 0.3 (T), and the magnetic field applied to its left kidney was about 1/10 of the above-mentioned magnetic field. Together with the left kidney and a kidney to which no field was applied (Control), a magnetic field was applied to the right kidney of the mouse; and after 10 minutes, the SNR was measured by MRI in T1 mode and T2 mode. As a result as shown in FIG. 4, it was confirmed that the magnetic crystals were successfully made to stay in the right kidney (RT) to which the magnetic field was applied, as compared to the left kidney (LT) and Control.

Figure 5:
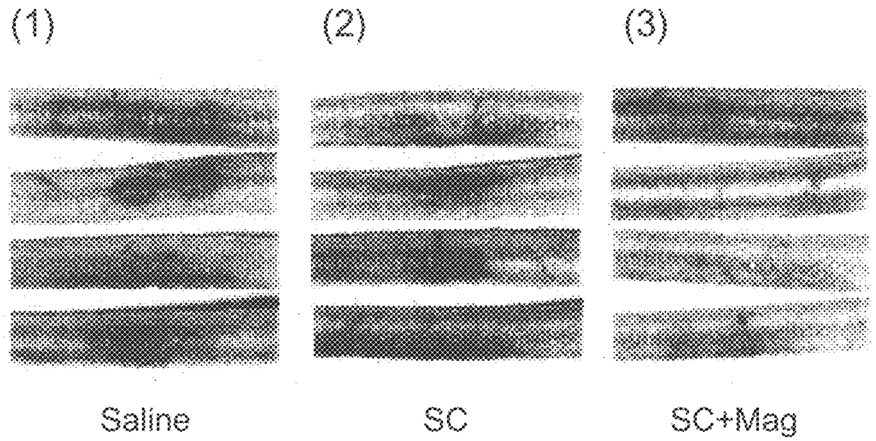
FIGS. 5(1), 5(2), and 5(3) are characteristic diagrams each showing depression effects of the magnetic substance on melanoma growth in mice.

FIG. 5 show the effect of the magnetic crystals on melanoma growth in mice. Melanoma was established in mouse tail tendons in vivo by local grafting of cultured melanoma cells (Clone M3 melanoma cells). Incidentally, FIG. 5(1) is a photograph showing effects of a saline group into which saline was injected instead of the magnetic crystals; FIG. 5(2) is a photograph showing effects of a group (SC) into which the magnetic crystals were injected without applying the magnetic field; and FIG. 5(3) is a photograph showing effects of a group (SC+Mag) into which the magnetic crystals were injected while applying the magnetic field (n=7 to 10).

The magnetic crystals 1 (50 mg/kg) were administered intravenously via tail tendon vein, followed by local application of a magnetic field by using a commercially available bar magnet (630 mT, a cylindrical neodymium magnet, 150 mm long and 20 mm in diameter). The bar magnet was made to gently contact the site of melanoma for 3 hours immediately after injection of the magnetic crystals. Application of the bar magnet was performed in such a way so that the magnetic field strength became maximal over an area of expected melanoma pigmentation, which was approximately 150 mm long, for a growth period of 2 weeks. Twelve days after the initial injection of the magnetic crystals, an extension of the melanoma was evaluated by assessing the size of melanoma pigmentation.

Figure 6:
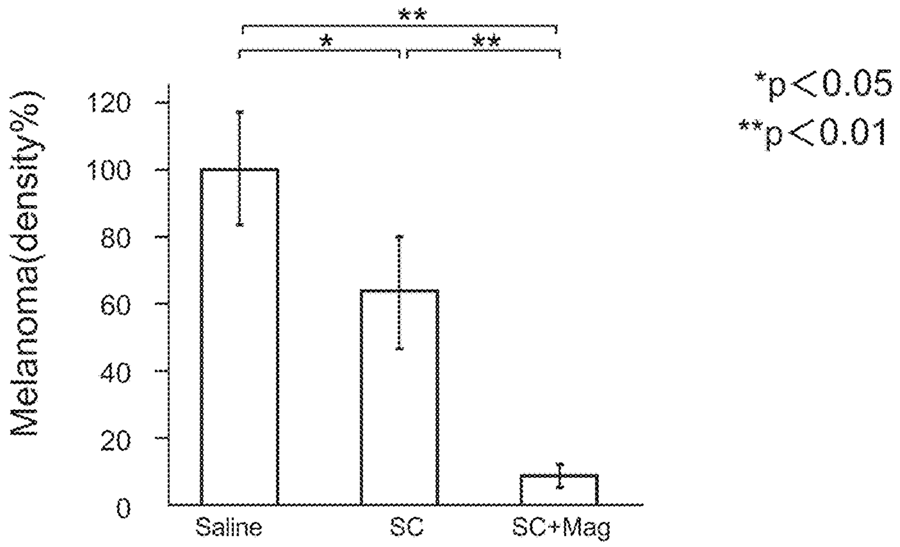
FIG. 6 is a graph illustrating changes of the size of melanomas.

As shown in FIG. 6, the melanoma extension was greatest (100±17.2%) in the saline group into which saline was injected instead of the magnetic crystals. Meanwhile, the melanoma extension modestly decreased (63.68±16.3%) in the SC group into which the magnetic crystals were injected without the application of a magnetic force field. In contrast, most melanoma disappeared (9.05±3.42%) in the SC+Mag group into which the magnetic crystals were injected while applying a magnetic field (n=7 to 10).

Figure 7:
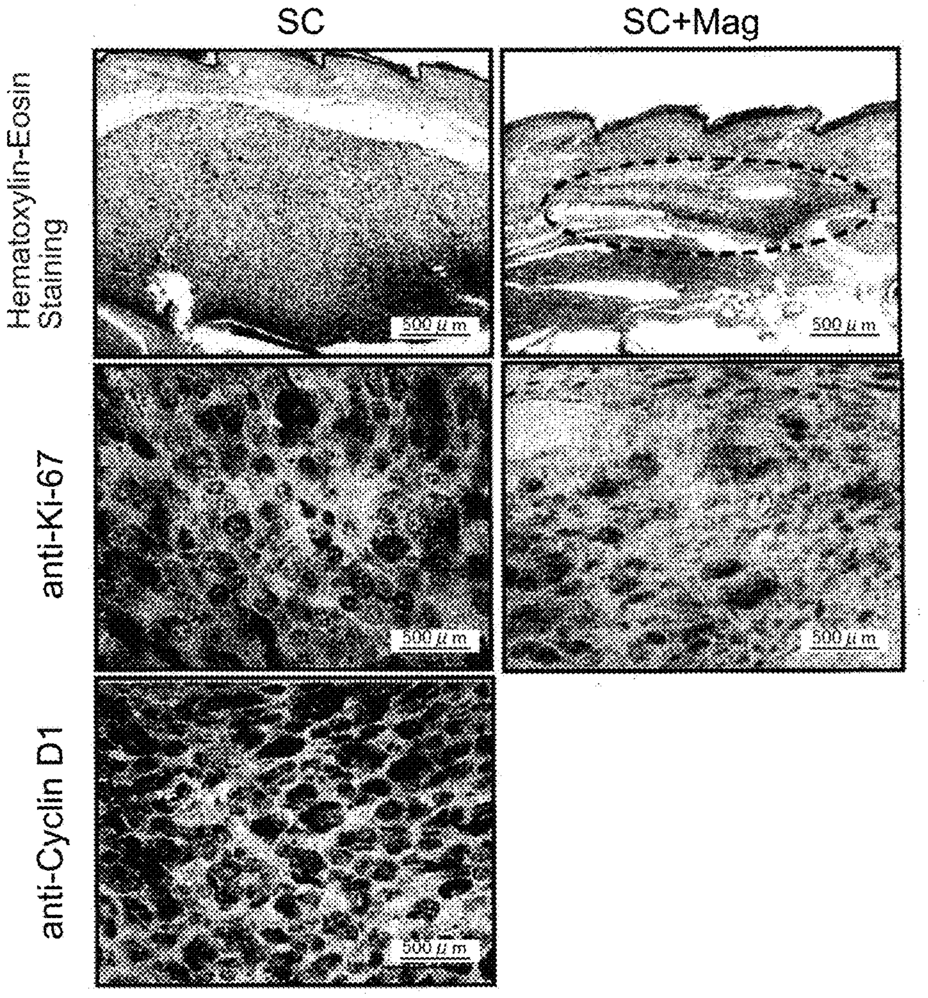
FIG. 7 is a characteristic diagram showing the results of a histological examination of melanomas.

A histological examination was performed as shown in FIG. 7 by means of Hematoxylin-Eosin staining and immunohistological staining with an anti-Ki-67 antibody and an anti-Cyclyn D1 antibody which are tumor proliferation markers. As a result, the histological examination revealed that tumor expansion of melanoma diminished when the magnetic crystals were injected (SC); and the tumor expansion of melanoma mostly disappeared when the magnetic field application was combined with administration of the magnetic crystals.

Figure 8:
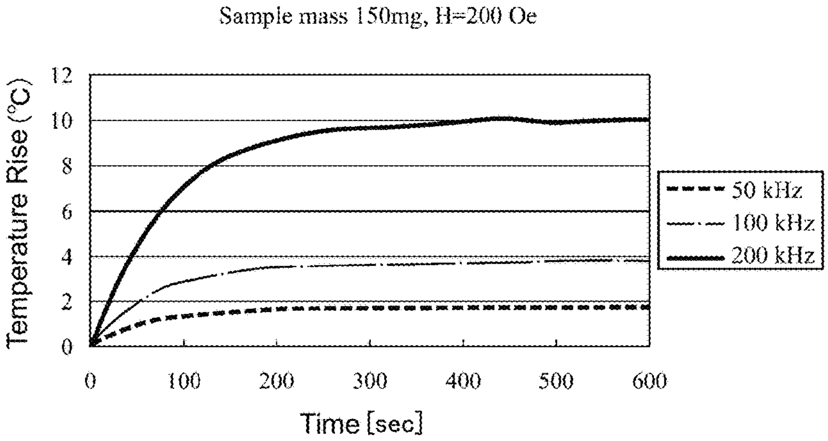
FIGS. 8(1), 8(2), and 8(3) each shows graphs of a temperature rise when an AC magnetic field is applied to the magnetic substance.
Figure 8:
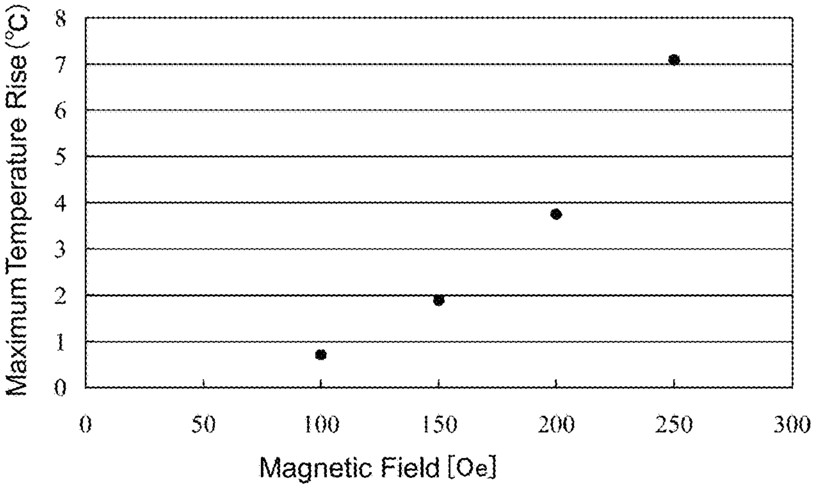
Figure 8:
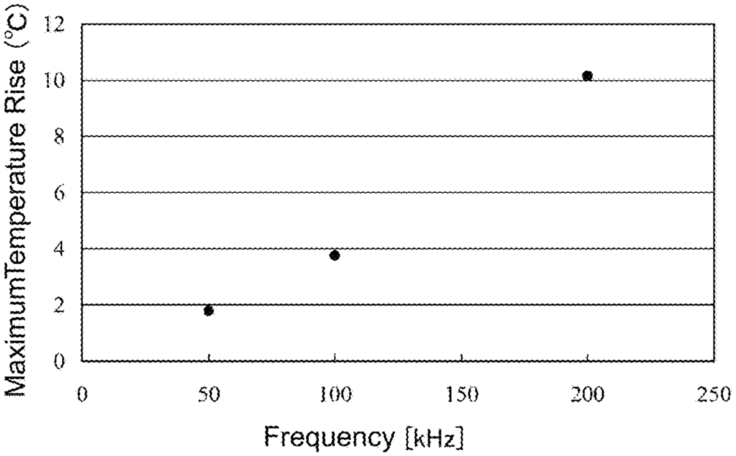

Furthermore, when an AC magnetic field with magnetic field intensity of 200 Oe and a frequency of approximately 50 kHz to 200 KHz was applied to 30 mg of magnetic crystals, the temperature of the magnetic crystals increased by 2 to 10 degrees Celsius (FIG. 8). As a result of conversion to temperatures at the time of administration into the body, it was confirmed that the above temperature range corresponds to 39 to 47 degrees Celsius, which was a temperature range capable of killing and damaging cancer cells. Incidentally, FIG. 8(1) shows temperature changes relative to time when the AC magnetic field was applied to the drug; FIG. 8(2) shows a maximum temperature when the frequency was fixed to 200 kH and only the magnetic field was changed; and FIG. 8(3) shows a maximum temperature when the magnetic field was fixed to 200 Oe and only the frequency was changed.

The invention claimed is:

1. A method for manufacturing a magnetic substance composed of crystals of a magnetization target compound and an electron acceptor compound, the method comprising:

combining the magnetization target compound with the electron acceptor, wherein the magnetization target compound is a metal-salen complex compound having a salen ligand;

forming a solution by dissolving a mixture of the magnetization target compound and the electron acceptor in a solvent;

cooling the solution to a very low temperature;

maintaining the solution in the very low temperature and allowing the solution to deposit the crystals of the magnetic target compound and the electron acceptor; and separating the crystals from the solvent, wherein the crystals are ferromagnetic organic crystals that maintain a structure of the magnetization target compound without damaging other properties of the magnetization target compound.

2. The method according to claim 1, wherein the electron acceptor is at least one of tetracyanoethylene (TCNE), tetracyanoguinodimethane (TCNQ), or anthryl derivatives, the anthryl derivatives being substances having an anthryl group.

3. The method according to claim 1, wherein the magnetization target compound and the electron acceptor form crystals of a charge transfer complex.

* * * * *